(12) United States Patent  
Jensen et al.

(10) Patent No.: US 8,679,160 B2
(45) Date of Patent: Mar. 25, 2014

(54) LAMINA IMPLANT SET

(75) Inventors: Harm-Iven Jensen, Noer (DE); Helmut D. Link, Hamburg (DE)

(73) Assignee: Facet-Link Inc., Rockaway, NJ (US)

( * ) Notice: Subject to any disclaimer, the term of this patent is extended or adjusted under 35 U.S.C. 154(b) by 43 days.

(21) Appl. No.: 13/246,533

(22) Filed: Sep. 27, 2011

(65) Prior Publication Data

US 2012/0095509 A1    Apr. 19, 2012

Related U.S. Application Data

(60) Provisional application No. 61/387,309, filed on Sep. 28, 2010.

(30) Foreign Application Priority Data

Sep. 28, 2010    (EP) ..................................... 10011329

(51) Int. Cl.
   *A61B 17/70*    (2006.01)
(52) U.S. Cl.
   USPC ......................................................... 606/248
(58) Field of Classification Search
   USPC ............... 606/246, 247, 248, 249, 282, 90, 60
   See application file for complete search history.

(56) References Cited

U.S. PATENT DOCUMENTS

2004/0193159 A1*  9/2004  Zucherman et al. ............ 606/61
2005/0251138 A1* 11/2005  Boris et al. ...................... 606/61
2008/0215096 A1*  9/2008  Nash et al. ..................... 606/249
2008/0319483 A1  12/2008  Triplett et al.
2010/0161056 A1*  6/2010  Voellmicke et al. ....... 623/17.11

FOREIGN PATENT DOCUMENTS

| CN | 101584601 | 11/2009 | |
| EP | 0 307 241 | 3/1989 | |
| EP | 0761175 | * 8/1996 | ................ 606/248 |
| EP | 0 761 175 | 3/1997 | |
| WO | WO-2006/073593 | 7/2006 | |
| WO | WO-2006/104487 | 10/2006 | |

OTHER PUBLICATIONS

European Search Report mailed May 19, 2011, directed to European Patent Application No. 10011329.9; 19 pages.

* cited by examiner

*Primary Examiner* — Pedro Philogene
(74) *Attorney, Agent, or Firm* — Morrison & Foerster LLP

(57) ABSTRACT

An implant set for insertion into the lamina of a vertebra includes several reinforcing implants, each of which includes a main body with bearing surfaces on the vertebra and a fastening device. The main body has a front surface, a rear surface, and lateral and medial side surfaces, the medial side surface being offset rearwardly in relation to the lateral side surface. The side surfaces bear on sectioned surfaces of the lamina, and a rearwardly protruding extension with a lateral bearing surface on a spinous process of the vertebra is arranged on the rear surface. In this way, the resection opening can be easily and safely closed. Sleeves can be provided for the fastening via screws that are oriented such that the screws are guided through the adjoining facets and fuse the latter.

31 Claims, 10 Drawing Sheets

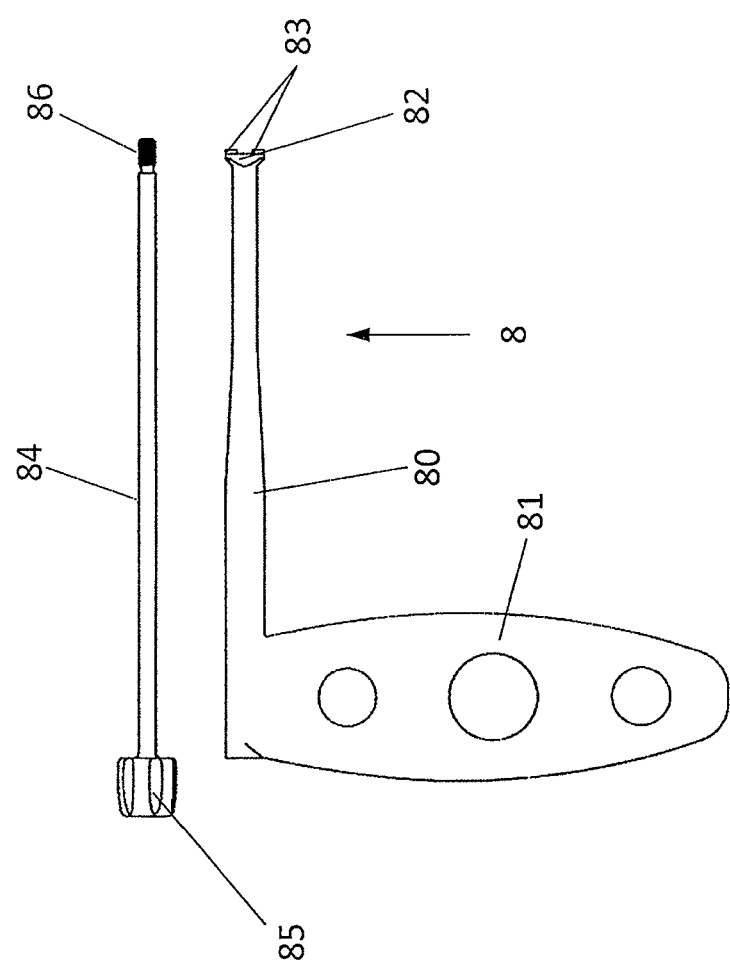

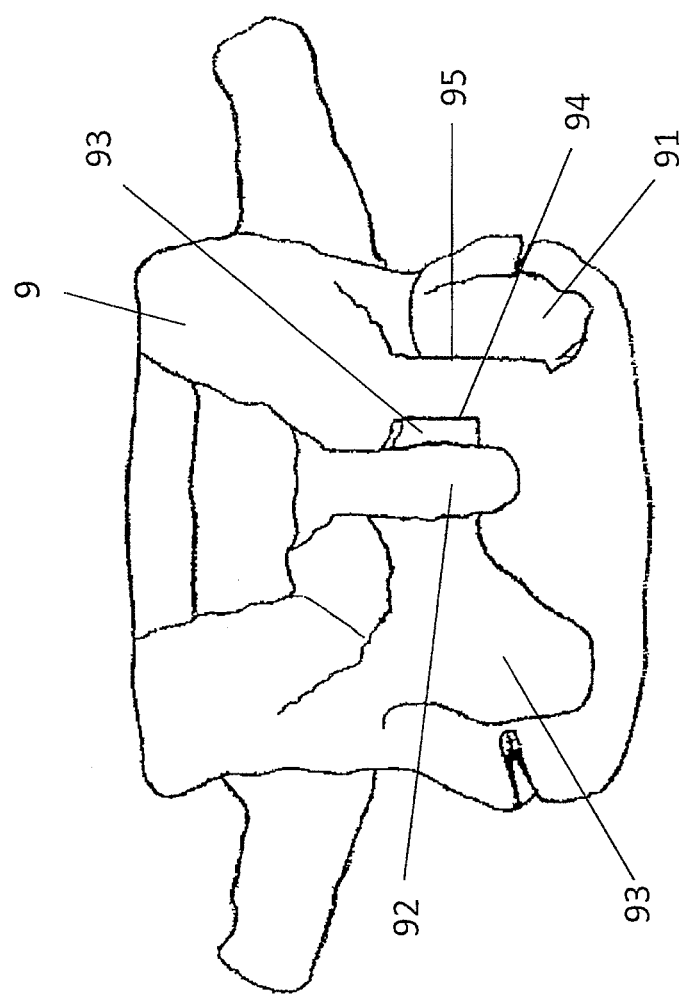

LAMINA IMPLANT SET

REFERENCE TO RELATED APPLICATION

This application claims the priority of European Patent Application No. 10 011 329, filed Sep. 28, 2010, and of U.S. Provisional Application No. 61/387,309, filed Sep. 28, 2010, the entire contents of which are incorporated herein by reference.

FIELD OF THE INVENTION

The invention relates to an implant set for the lamina of a vertebra, comprising several implants that each comprise a main body with bearing surfaces on the vertebra and a fastening device.

The spinal column in humans comprises a multiplicity of vertebrae arranged in a load-bearing manner one above another and interconnected in an articulated manner. The vertebrae differ in shape depending on where they are located in the spinal column, but they nonetheless have some features in common. Thus, each vertebra has a solid vertebral body with two osseous projections (pedicles) which extend laterally and to the rear and which, in their rear part, are connected by an osseous arch. In the connection area, the osseous arch is shaped as a broad plate (lamina) and has, at its center, a rearwardly protruding spinous process. The spinous process and two further transverse processes on the side surfaces of the pedicles form articulation points for muscles and ligaments. In the area where the pedicles merge into the broad lamina, an upper and a lower articulating process are arranged on each side. These each form part of a facet joint (zygapophyseal joint) with an adjacent upper or lower vertebra. A vertebra is also connected to its adjacent upper and/or lower vertebra via an intervertebral disk, the latter being arranged at the bottom and/or top on the relatively flat cover surfaces of the vertebral body. The space bounded by the rear side of the vertebral body and by the vertebral arch forms a hollow space in which nerve fibers running parallel to the spinal column are accommodated.

Many different forms of back pain can occur as a result of disease or injury. These can be caused in particular by defects of the intervertebral disk or of the facet joints and/or by the nerve fibers extending through the hollow space becoming pinched or trapped. In the latter case, it is known that pressure exerted on the nerve fibers by protrusions of the intervertebral disk or by osseous growths in the area of the hollow channel can be avoided by removal of these protrusions and/or growths. For this purpose, an access route to the hollow space is created through the rear side of the vertebral arch, that is to say generally through the lamina, and the growths causing the problems are removed from there by means of suitable instruments known per se. In this way, the pressure is removed from the nerve fibers, whereupon the pain induced by the pressure is correspondingly reduced. In this method, also known as laminectomy or decompression, the access created in the lamina, that is to say the opening present therein, is in most cases not closed after the operation. It has been shown that this weakens the mechanical stability of the vertebra.

BACKGROUND OF THE INVENTION

The object of the invention is to reduce or avoid the occurrence of these ensuing problems.

The solution according to the invention lies in the features broadly disclosed herein. Advantageous developments of the invention are the subject matter of the detailed disclosure.

An implant set comprises several reinforcing implants for insertion into the lamina of the vertebra, which reinforcing implants each comprise a main body with bearing surfaces on the vertebra and a fastening device, wherein according to the invention the main body has a front surface, a rear surface, and medial and lateral side surfaces, wherein the medial side surface is offset rearwardly in relation to the lateral side surface, and the medial and lateral side surfaces are designed to bear on sectioned surfaces of the lamina, and wherein a rearwardly protruding extension with a lateral bearing surface on the spinous process is arranged on the rear surface, and wherein the reinforcing implants of the set differ from one another in terms of the distance between medial side surface and lateral side surface.

The invention is based on the concept of making available a plurality of block-like reinforcing implants which differ in terms of their thickness, so as to be able to fill and reliably close resection openings of different widths in the lamina. The fastening device ensures that the reinforcing implant is fixed securely in its position in the lamina. By virtue of the reinforcing implant, the vertebral arch interrupted by the resection opening is completely closed again. Not only does this provide better protection for the nerve fibers running in the hollow channel, the mechanical stability of the vertebral arch is also restored and recovers the original values at the very latest when the implant has become incorporated.

The invention in this respect exploits the fact that, in the unilateral resection that is performed particularly often in practice (this is understood to mean access through the lamina only on one side, that is to say either to the left or right of the spinous process), sufficiently extensive and mechanically stable fastening to the spinous process is possible, and this possibility is made use of to fasten the reinforcing implant according to the invention. The claimed shape with the mutually offset side surfaces, which bear on the resected surfaces of the lamina after the resection, ensures a geometrically favorable integration of the reinforcing element in the vertebral arch, specifically in such a way that the reinforcing implant does not cause problems by protruding into the hollow space for the nerve fibers and also does not extend substantially outward. In other words, the main body of the reinforcing implant remains substantially inside the area that was filled by the corresponding part of the lamina prior to the resection. The danger of undesired irritation of the nerve fibers inside the hollow channel and also of the surrounding tissue is thus effectively countered.

A further advantage of the reinforcing implant according to the invention is that, after the correct reinforcing implant has been chosen from the set, only this part has to be inserted, and no other assembly work or adjustment work is needed deep within the operating site. It suffices to insert the implant of appropriate size and to fix it at the intended location by means of the fastening device, in the simplest case a bone screw. This ease of implantation thus safeguards against incorrect implantation and thereby contributes directly to improved outcomes.

Although the side surfaces are in most cases parallel to each other, they can form a wedge shape tapering slightly toward the front, the wedge angle measuring between 0 and 20°. The wedge angle is preferably less than 10°, more preferably less than 5°.

By virtue of the mutually offset arrangement of the side surfaces, the front surface and rear surface are oblique with respect to the two side surfaces, and they are in fact preferably substantially parallel or deviate from this by a maximum of 20°.

Advantageously, the side surfaces are not only mutually offset toward the front and rear, but also upward and downward. The main body thus expediently has a rhomboidal shape in two different planes. The rhombus angle (smaller internal angle) is here preferably between 35 and 75° in the vertical with respect to the underside and 30 to 60° in a plane orthogonal to the rear surface.

The lateral surface arranged further forward preferably forms a rounded apex angle with the front surface. This facilitates the insertion of the main body into the opening created by the resection, since the rounding prevents the implant from catching on the lamina in the event of an uneven shape of the resected surfaces, and the acute angle facilitates insertion, if appropriate with slight elastic widening (to achieve what is called a press fit), to the full thickness.

In order to avoid the reinforcing implant being inserted too far into the hollow space, a shoulder-shaped projection is preferably formed on one side surface and functions as an abutment. This ensures that a secure fit of the implant at the intended location can be achieved even without close visual monitoring and, in particular, it avoids a situation where the implant is pushed in too far and exerts pressure on the nerve fibers located in the hollow space. The danger of operating errors is thus effectively countered. It has proven useful that the shoulder-shaped projection is located at a distance from the front surface corresponding to approximately 0.8 to 2.2 times the thickness of the main body. It has proven useful to have a linear relationship with offset, such that, starting with a thickness of 3 mm, the distance is 6 mm, and the distance increases by 0.5 mm for each 1 mm of additional thickness.

A fastening hole is expediently provided on the rearwardly protruding extension. This not only provides securing by means of the lateral bearing surface and the force-fit thereof on the spinous process, it is also possible to achieve a form-fit fastening to the spinous process by insertion of a suitable fastening means (for example a screw). For this purpose, the fastening hole is preferably designed for the polyaxial reception of a screw. This is understood to mean that the screw with its head has a secure planar contact in the area of the fastening hole not only in an exactly central position, but also at angular deviations of up to 15° in each direction. In this way, even with a different anatomy of the vertebra, the screw can always be fitted in an orientation favorable for the fastening, preferably a translaminar screw. With this, a particularly secure hold can be achieved in the intact part of the lamina lying on the other side of the spinous process. However, a screw connection can also be provided directly on the spinous process; this is generally recommended when the opposite part of the lamina also has a defect. For this purpose, a screw dowel device is advantageously used. It permits secure fastening even in the case of a thin spinous process and in all situations in which, because of the small size of the fastening means used here, sufficiently reliable transfer of force would not be guaranteed by the screw thread alone. It comprises a dowel and a dowel screw. The dowel is preferably of sleeve-shaped configuration, with several segments which are connected at a near end and are free at their far end and have outwardly facing retainer hooks. They are dimensioned such that, when the dowel is pushed into the spinous process, they emerge on the other side and there engage behind the edge of the opening. The retainer hooks are preferably arranged in several steps with a height increasing toward the fixed end, in order to achieve a secure hold in spinous processes of different thicknesses.

The medial and lateral side surfaces are preferably provided with spikes. Proven shapes of the spikes are conical tips, pyramids, prismatic V-shaped elevations of different extent and height. They are advantageously configured asymmetrically, specifically in such a way that they have a greater bevel toward the front than in the opposite direction. This makes the implant easier to insert and provides a barb effect against undesired rearward migration. Secure primary fixation can be achieved in this way. In order to additionally increase the secondary fixation, the medial and lateral side surfaces are preferably provided with a coating that promotes bone growth. This can in particular be hydroxyapatite or other osteoinductive substances.

A laterally protruding fixing tongue is preferably provided on the rear edge of the lateral side surface. It is designed such that, in the implanted state, it rests on an outer surface of the so-called pars. In order to achieve good contact independently of the individual anatomy, the angle of the fixing tongue to the lateral side surface can preferably be changed. This can be achieved in practice, in a particularly expedient manner, by a flexible design of the fixing tongue, preferably with a reduced material thickness in the area of the transition between fixing tongue and main body. The fixing tongue can have a fastening hole, which advantageously has several defined receiving positions for a second fastening element, in particular a pars screw. The defined receiving positions make it possible to provide different positions for the pars screw in relation to the fixing tongue, wherein the pars screw is mounted with a form fit in each position, which is not the case in an oblong hole. As is also the case in the fastening of the translaminar screw, the receiving positions of the fixing tongue are preferably designed for polyaxial reception of a screw. In this way, the pars screw can be arranged not only with a translational degree of freedom but also with two rotational degrees of freedom in relation to the fixing tongue, which permits reliable fastening even in difficult anatomical situations. The angle range for the polyaxial receipt of the screw preferably once again measures approximately ±15° in each direction.

The reinforcing implant preferably has a tool receiver on its rear surface. This tool receiver allows the reinforcing implant to be received and held securely on a tool serving for the implantation. It is thus made easier for the operating surgeon to bring the reinforcing implant safely and precisely to the intended implantation site and to fasten it in place there. For this purpose, the tool receiver preferably has a longitudinal groove. This can be in one part or can be formed from several (also round) recesses. An unambiguous orientation of the reinforcing implant with respect to the tool can thus be achieved. A pulling thread is advantageously formed at the bottom of the tool receiver. It is thus possible, in combination with a holding screw on the tool, to secure the reinforcing implant on the tool and thereby not only to protect it against falling out and being lost, but also maintain it in a correct angular orientation.

A holding tool is preferably provided for this purpose, specifically such that it has a foot with an elongate gripper foot designed for interaction with the tool receiver. This gripper foot comprises, at the front end, a protruding area designed for complementary engagement in the longitudinal groove. It preferably comprises a connection of the gripper foot to a handle on a long hollow shaft through which a clamping element is guided that engages in the pulling thread. In this way, from the handle, the reinforcing implant can be clamped firmly on the gripper foot for safe implantation and, when the implantation site is reached, can be released therefrom, without the surgeon having to work deep within the operating site. It has proven useful in practice to arrange, at the rear end of the hollow shaft, a laterally extending projection, which has a predefined orientation with respect to the elongate gripper foot. The projection can preferably be a part of the grip. Thus, by taking hold of the instrument, it is already clear to the operating surgeon in which orientation the reinforcing implant clamped on the gripper foot is located. The danger of incorrect implantation as a result of incorrect orientation is thus reduced.

The material provided for the reinforcing implant is preferably a titanium alloy or pure titanium. This has the advantage of a high degree of biocompatibility in combination with good mechanical processing and load-bearing. Other materials that have proven useful are alloys of titanium/aluminum/vanadium, titanium/niobium/vanadium or cobalt/chromium/molybdenum, and also biocompatible plastics, such as polyether ether ketone (PEEK), or combinations of these materials.

The main bodies of the set according to the invention have different distances between medial side surface and lateral side surface (this distance is designated as the thickness). A range of between 3 and 15 mm has proven useful, and it has proven sufficient in practice to provide a gradation of in each case 2 mm. A millimeter gradation can also be provided for a finely graduated implant set.

The set according to the invention preferably additionally comprises mirror-inverted implants, which are likewise provided in different thicknesses. A treatment adapted to the anatomy can in this way be provided both in the left-hand area and also in the right-hand area of the lamina.

BRIEF DESCRIPTION OF THE DRAWINGS

The invention is explained below on the basis of advantageous illustrative embodiments and by reference to the attached drawing, in which:

FIG. 6 shows an instrument for the implantation;

FIGS. 7a-c show a vertebra with a resected lamina and with an inserted implant in a rear view from below.

DETAILED DESCRIPTION OF THE INVENTION

Figure 1:
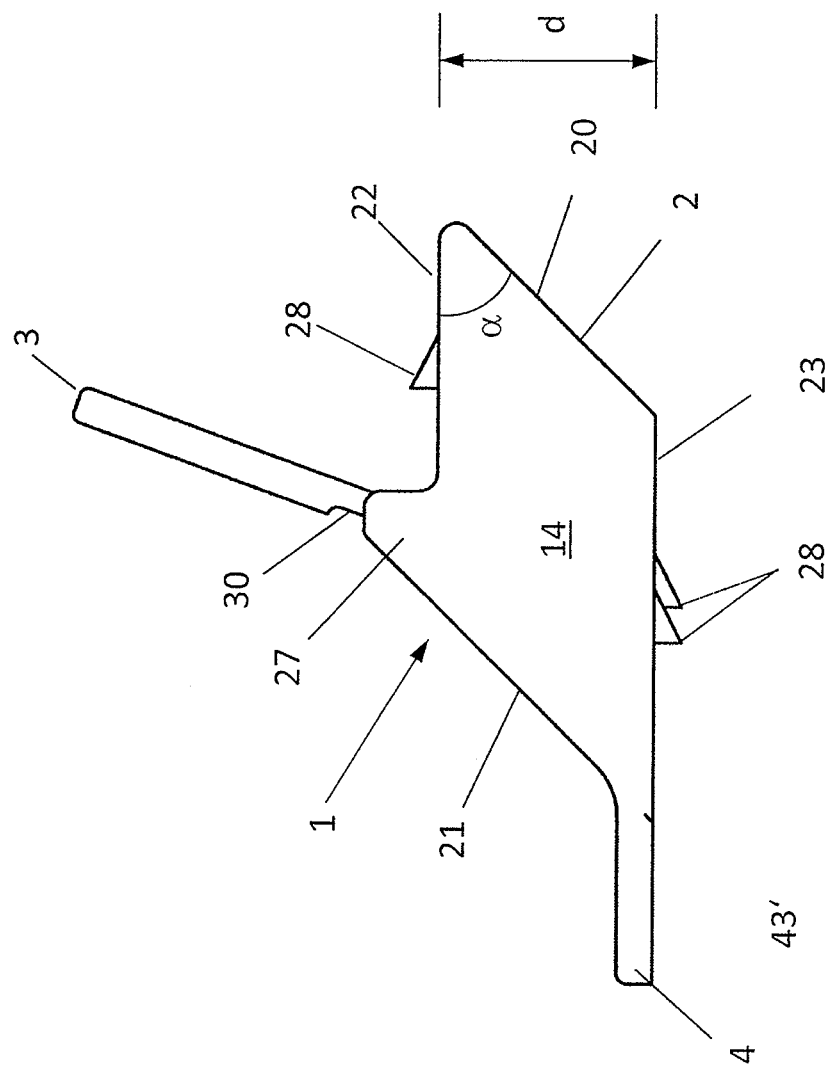
FIG. 1 shows a bottom view of a first illustrative embodiment of a right-hand reinforcing implant.
Figure 2:
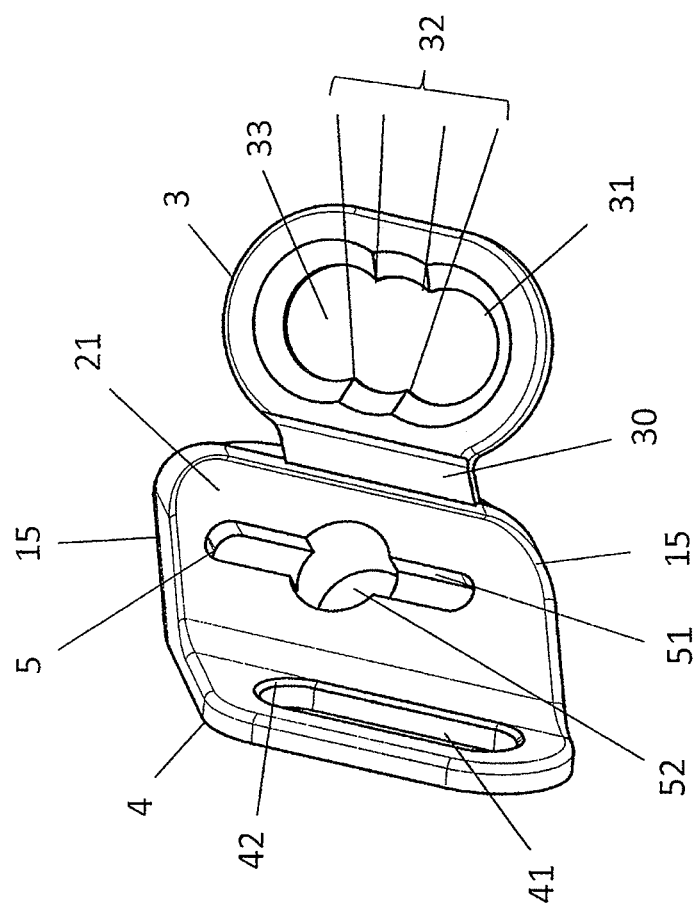
FIG. 2 shows a view, obliquely from behind, of the illustrative embodiment shown in FIG. 1.

FIG. 1 depicts a first illustrative embodiment of a reinforcing implant according to the invention, which is designated in its entirety by reference number 1. It has a forwardly facing oblique front surface 20, a rearwardly facing and similarly oblique rear surface 21, and also a lateral side surface 22 and a medial side surface 23. An underside 14 and, opposite the latter, a top surface 15 (see FIG. 2) are also provided, which merge via rounded edges into the front surface 20. These surfaces delimit a main body 2, which has a double rhomboidal shape.

The front surface 20, the rear surface 21 and the two side surfaces 22, 23 form a rhombus with a rhombus angle α of 45° measured in a plane orthogonal to the rear surface 21. (Rhombus angle is understood as the smaller of the internal angles.) The lateral and medial side surfaces 22, 23 are oriented parallel to each other, although this does not rule out the possibility of their forming a wedge angle. The front surface 20 and the rear surface 21 are likewise arranged parallel to each other. There is also a rhomboidal shape with respect to the front surface 20, rear surface 21, underside 14 and top surface 15 (see FIG. 2). Here, the rhombus angle β measures approximately 55°. Arranged on the side surfaces 22, 23, there are spikes 28 which are for primary fixation and are beveled toward the front.

At the rear end of the medial side surface, a rearwardly protruding extension 4 is arranged in the area of the transition to the rear surface 21. This extension 4 has, on its medial side, a bearing surface 43 for bearing on the spinous process of a vertebra. The bearing surface 43 and the medial side surface 23 are preferably in one plane. The extension is relatively thin and has a material thickness of up to 1.5 mm.

An abutment shoulder 27 is formed in the area of the transition between the lateral side surface 22 and the rear surface 21. The rearwardly facing side is oblique and forms a plane with the rear surface 21, while its forwardly facing side is oriented perpendicular to the lateral side surface 22. It thus forms, with its front side, an abutment which limits the depth of insertion of the implant into the resection opening. The implant is inserted until the abutment shoulder 27 rests with its front side on the bone of the lamina.

Figure 5:
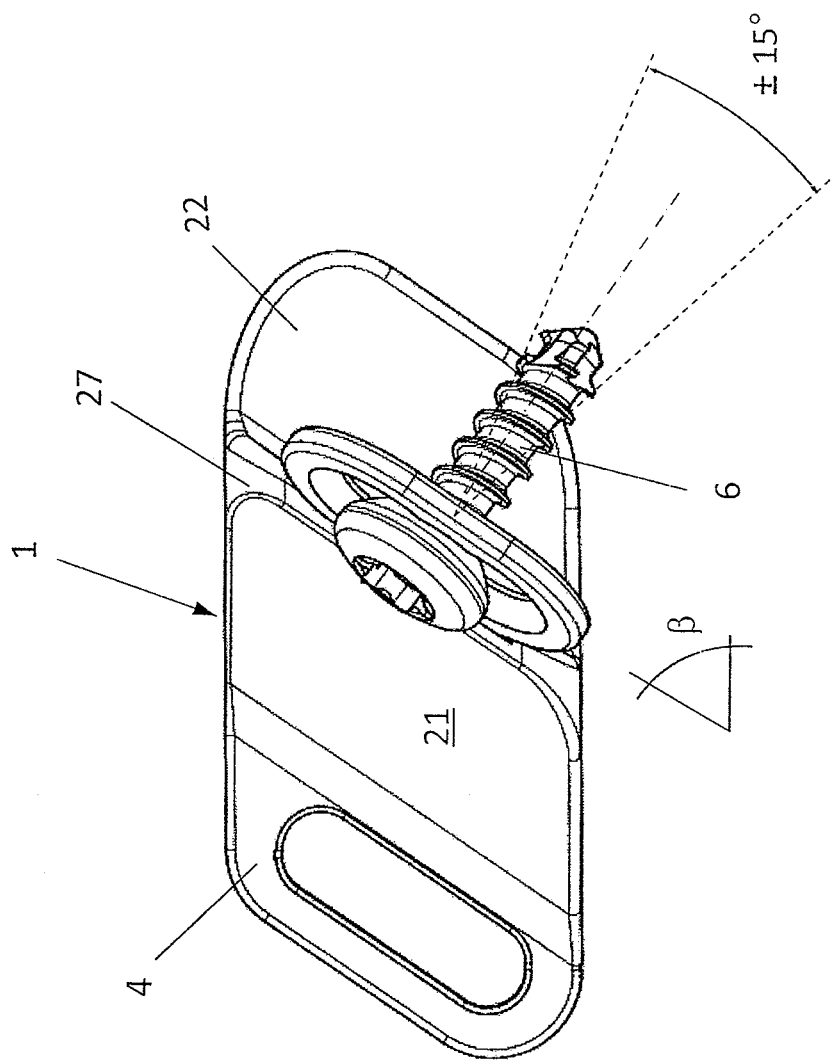
FIG. 5 shows a view from the right with inserted fastening screw.

A fixing tongue 3 is articulated on the abutment shoulder 27. It has a substantially oval configuration and is mounted bendably, via a portion of reduced material thickness 30, on the abutment shoulder 27 of the main body 2. The fixing tongue 3 has a similar opening 31 which, on its two long sides, is divided into three areas by two projections 32. The edge of the opening is shaped obliquely such that, together with the projections 32, a conical contact surface is formed for a round receiving head, which can be mounted in a total of three positions in the opening 1: an upper position, a middle position between the pairs of projections 32, and a lower position. They serve to receive a pars screw (see FIG. 5). The pars screw 6 is mounted in a receiving position 33 in the opening 31 of the fixing tongue 3 such that it can adopt different axes (polyaxial) through ±15° in two directions. On account of the different receiving positions 33, the pars screw 6 can be moved by 4 mm in the opening 31.

Figure 4:
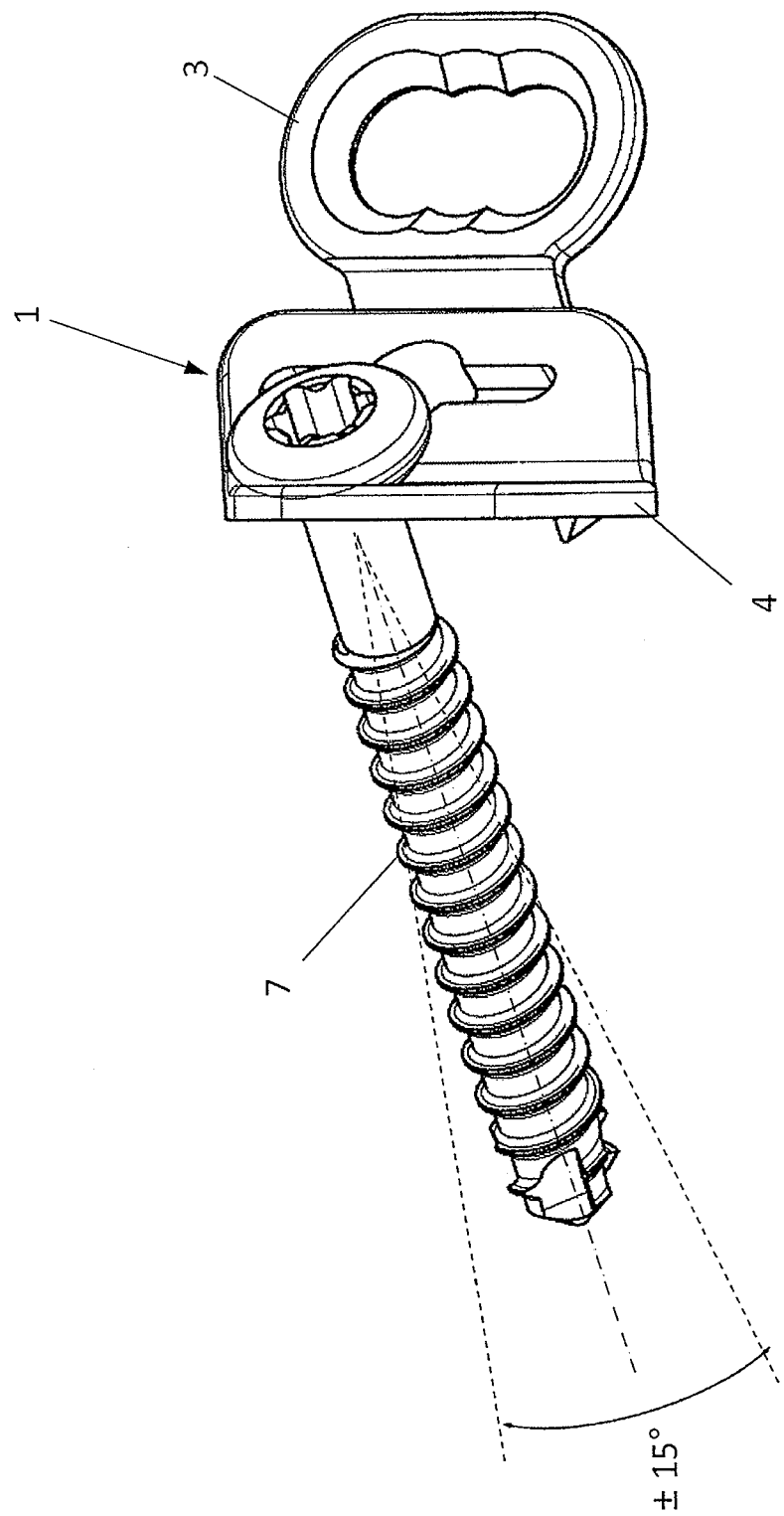
FIG. 4 shows a rear view with inserted fastening screw.

A similar polyaxial seat for a laminar screw 7 is provided in the extension 4. For this purpose, an opening 41 is formed which, at its edge 42, likewise has bevels in order to permit, together with the screw head, a polyaxial mounting about ±15° (see FIG. 4). The opening 41 is designed as an oblong hole and allows the laminar screw to be arranged in different positions along a length of 3.5 mm.

Moreover, a tool receiver 5 is arranged in the rear surface 21. It comprises a longitudinal groove 51 with a blind hole, which is arranged in the middle of the groove bottom and has a pulling thread 52. The longitudinal groove 51 receives, at the correct angle and in a manner secure against rotation, the gripper foot of a holding tool, onto which the implant is drawn via the pulling thread 52 by a clamping screw contained in the tool.

An embodiment of a corresponding instrument 8 is shown in FIG. 6. It comprises an elongate shaft 80, which is provided with a hollow bore along the central axis. A laterally protruding handle 81 is arranged at one end and is fixed in terms of its angle to the hollow shaft 80. At the other end of the hollow shaft 80, there is a gripper foot 82 which, at its outer end, has a ridge extending transversely with respect to the axis of the hollow shaft 80. The ridge is shaped in such a way that, with respect to its length and width, it can be introduced into the complementary seat in the longitudinal groove 51 of the main body 2. A clamping screw 84 with a rotary grip 85 at the handle end and with a threaded head 86 at the opposite end is fitted in the hollow shaft 80. The threaded head 86 is designed such that it engages in the thread 52 at the bottom of the longitudinal groove 51 and clamps this against the gripper foot. In this way, the implant 1 is mounted on the instrument 8 firmly and in a manner secure against rotation. Through suitable orientation of the handle 81, the operating surgeon knows exactly at what angle the implant 1 is located and can insert the latter in a targeted manner, specifically until the abutment shoulder 27 prevents further insertion. The implant 1 is thus positioned. All that then has to be done is, using suitable drills and screwdrivers, to insert the pars screw 6 and laminar screw 7 that are required for further fastening.

Figure 7B:
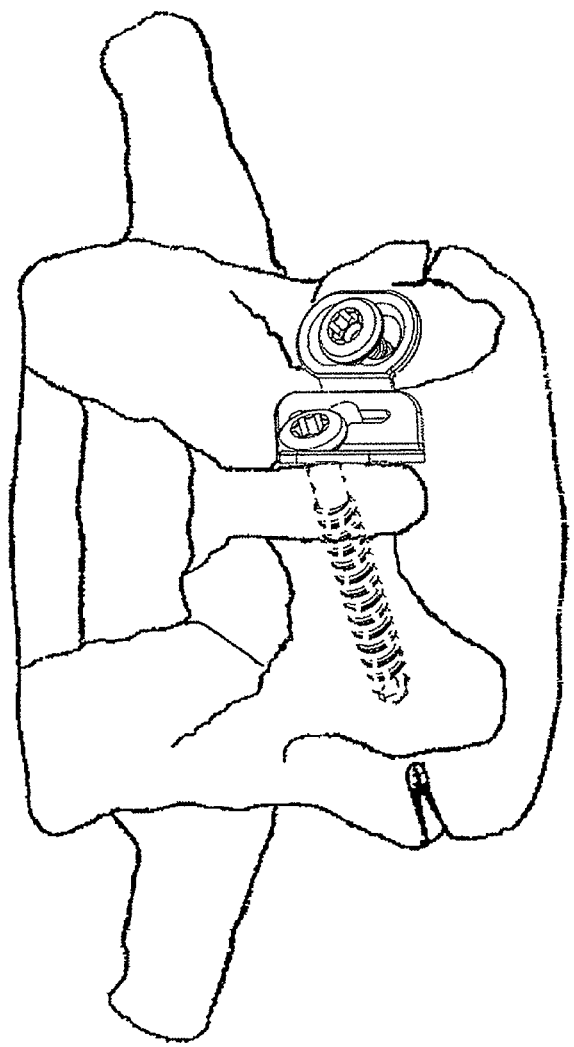
Figure 7C:
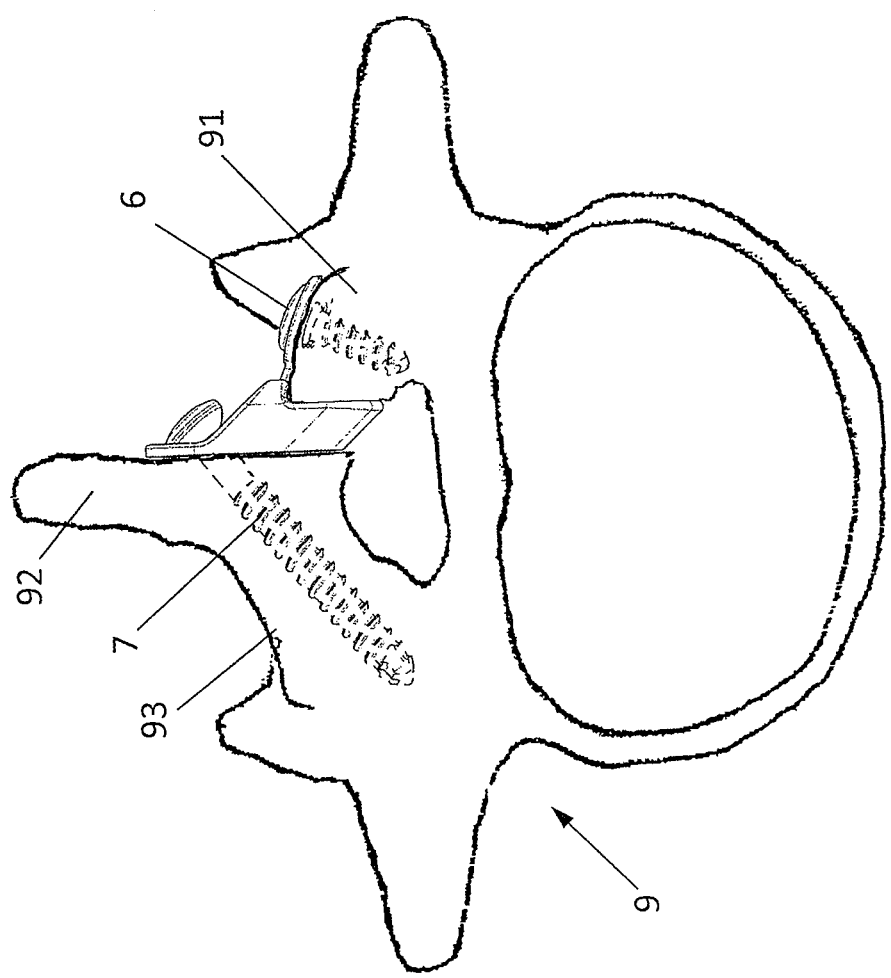

FIGS. 7a-c show an example of the arrangement of the implant in a vertebra 9. FIG. 7a is a rear view of the vertebra 9 showing a resection in the area of the lamina 93, more precisely in the area to the right of the spinous process 92. Sectioned surfaces 94, 95 can be seen that have been made on the left and right edges of the opening. The implant 1 is inserted into this opening by means of the instrument 8 in the manner described above. The implant 1 is chosen from the set (see FIG. 3), in terms of its thickness d, such that it completely fills the space between the two sectioned surfaces 94, 95 of the lamina. The spikes 28 on the lateral and medial side surfaces 22, 23 of the main body 2 engage in the sectioned surfaces 94, 95 and thus provide primary fastening of the implant. In order to further protect the implant against migration and against twisting, further anchoring is provided by the pars screw 6 in the pars interarticularis 91 of the vertebra 9 and by means of the laminar screw 7 in that part of the lamina 93 located on the other side of the spinous process 92. The arrangement of the screw is symbolized for illustrative purposes in the partially cutaway view in FIG. 7c.

Figure 8:
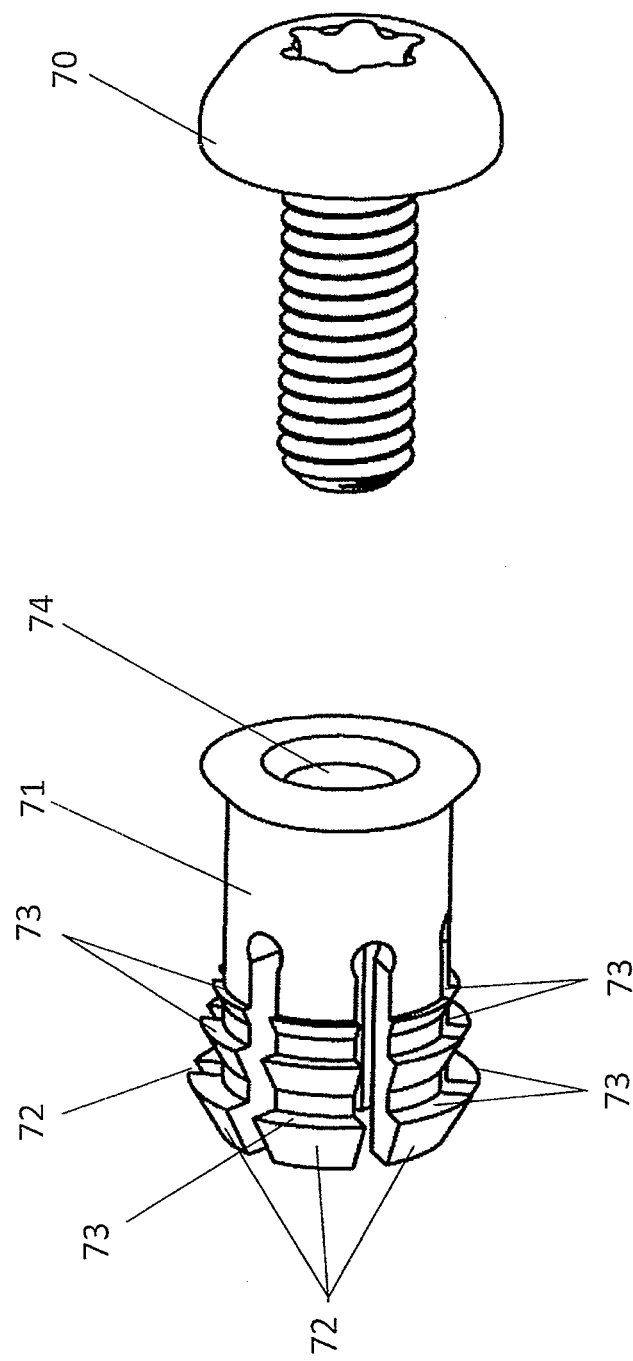
FIG. 8 shows a fastening means according to a second illustrative embodiment.

An alternative means of fastening using a screw dowel device is shown in FIG. 8. It comprises a dowel 71 with several segments 72 that are divided by longitudinal slits and that are connected to one another at one end and are free at the other end. Arranged at each free end, there is an outwardly facing retainer hook 73, which is designed to engage behind the opening edge of the bore through which the dowel is plugged. In order to achieve sufficiently secure engagement even in through-bores of different lengths, the retainer hook is preferably designed in several steps (with three steps in the illustrative embodiment shown). Each step has a lower height than the adjacent one lying further to the outside. The dowel is also provided with an internal thread 74. A fixing screw 70 provided with a corresponding external thread engages in the internal thread and is inserted, instead of the laminar screw 7, through the opening 41 in the extension 4. Secure anchoring on the spinous process 92 can be achieved in this way.

Figure 3:
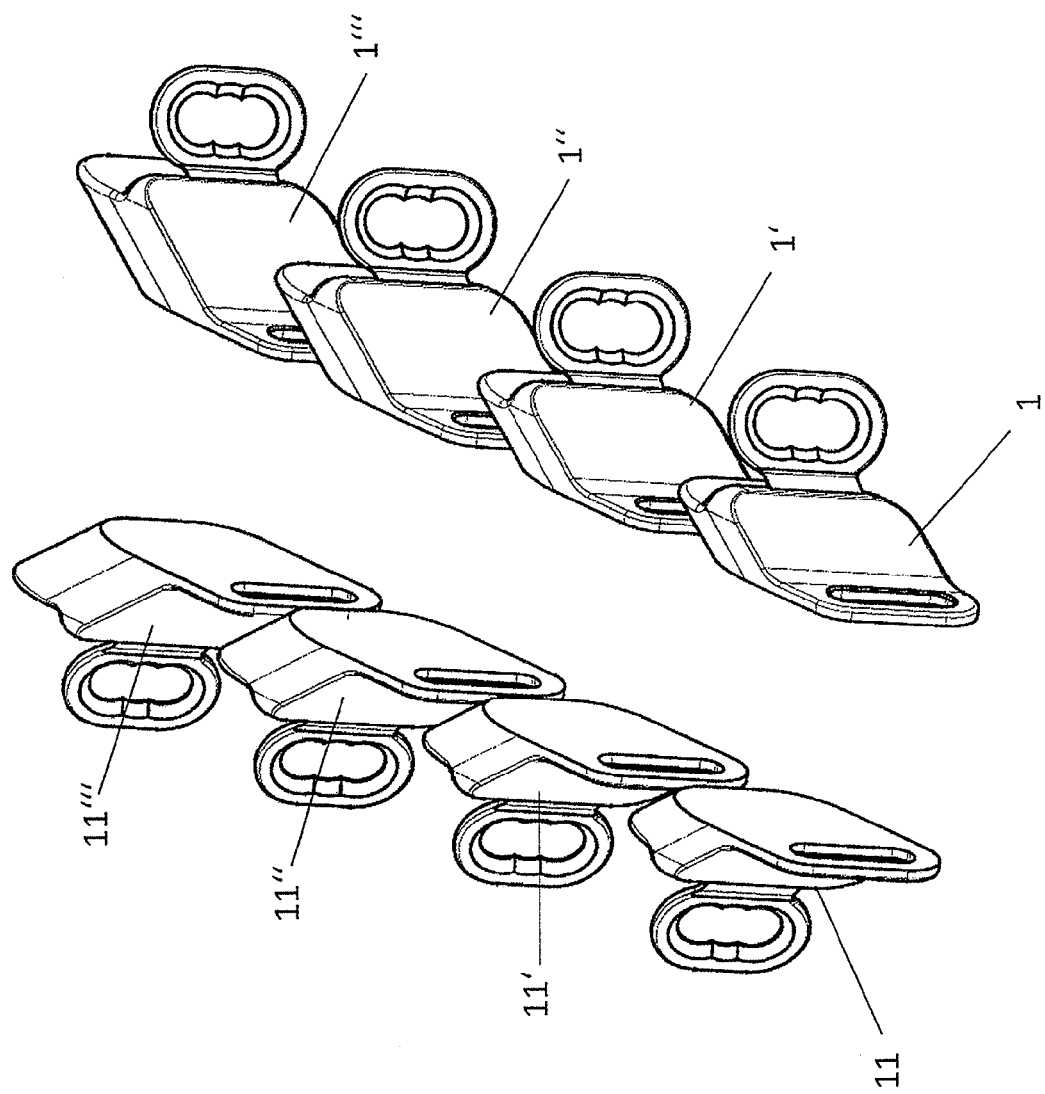
FIG. 3 shows a set with reinforcing implants of different thickness.

Examples of implants 1 in different sizes are shown in FIG. 3. The implants 1, 1', 1'', 1''' are substantially identical and differ only in respect of their thickness d, that is to say the distance between lateral side surface 22 and medial side surface 23. They also differ in terms of the distance of the front side of the shoulder 27 from the rounded front edge of the lateral side surface 22 which, in the illustrative embodiment shown, is approximately 0.9 times the thickness d. The set further comprises similar but mirror-inverted implants 11, 11', 11'', 11''', which together form an implant set 11. In this way, dedicated implants adapted to the anatomy can be used for implantation in the lamina on the left-hand side and on the right-hand side.

The individual steps involved in the implantation are outlined below. After an opening has been created (cf. FIG. 7a), a test implant is used to determine the width of the opening and therefore the suitable size of the implant 1 from the implant set according to the invention. The test implant also comprises sample bores on the extension 4 and on the fixing tongue, in order to form bores for receiving the pars screw 6 and the laminar screw 7 using the test implant as drill jig. In a next step, the implant is mounted and secured on the tool 8 in the manner shown and, finally, inserted into the resected space in the lamina 93. The fastening devices used for securing, particularly in the area of the extension 4, are introduced. The implant is definitively secured by tightening of the fastening screws.

The invention claimed is:

1. An implant set configured for insertion into the lamina of a vertebra, comprising:
a plurality of reinforcing implants, each comprising a main body with bearing surfaces configured to bear on the vertebra and a fastening device, wherein the main body has a front surface, a rear surface, a lateral side surface and a medial side surface, wherein the lateral and medial side surfaces are arranged on opposite sides and face outwards of the main body, the medial side surface is offset rearwardly in relation to the lateral side surface, and the side surfaces are configured to bear on sectioned surfaces of the lamina, and a rearwardly protruding extension with a lateral bearing surface on a spinous process of the vertebra is arranged on the rear surface.

2. The implant set of claim 1, wherein the side surfaces are oriented parallel to each other or in a wedge-shaped formation, wherein a wedge angle between the side surfaces measures between 0 and 20°.

3. The implant set of claim 1, wherein the front surface and the rear surface are at an oblique angle to both side surfaces and are oriented approximately parallel to each other.

4. The implant set of claim 1, wherein the main body has a rhomboidal shape in two planes.

5. The implant set of claim 4, wherein a rhombus angle $\alpha$ measures between 35 and 75° in a vertical direction, and a rhombus angle $\beta$ measures between 30 and 60° in a plane orthogonal to the rear surface.

6. The implant set of claim 1, wherein the lateral side surface forms a rounded apex angle with the front surface.

7. The implant set of claim 1, wherein a shoulder-shaped projection is formed on one side surface and functions as an abutment.

8. The implant set of claim 7, wherein the projection is arranged at a distance from the edge to the front surface, which distance increases linearly with increasing thickness.

9. The implant set of claim 1, wherein a fastening hole is provided on the extension.

10. The implant set of claim 9, wherein the fastening hole is configured for the polyaxial reception of a screw.

11. The implant set of claim 10, wherein the fastening device comprises a translaminar screw.

12. The implant set of claim 10, wherein the fastening device is configured as a screw dowel device with a dowel and with a dowel screw engaging the dowel.

13. The implant set of claim 12, wherein the dowel has several segments, which are connected at one end and which, at their other end, are free and have outwardly acting retainer hooks.

14. The implant set of claim 13, wherein the retainer hooks on the segments are arranged in several steps with a height increasing toward the fixed end.

15. The implant set of claim 1, wherein the side surfaces are provided with spikes having a greater bevel toward the front than toward the rear.

16. The implant set of claim 1, wherein the side surfaces are provided with a coating that promotes bone growth.

17. The implant set of claim 1, wherein a tool receiver is arranged on the rear surface.

18. The implant set of claim 17, wherein the tool receiver has a longitudinal groove.

19. The implant set of claim 18, wherein a pulling thread is formed at the bottom of the longitudinal groove.

20. The implant set of claim 18, wherein a holding tool is provided, which has a gripper foot configured to interact with the longitudinal groove.

21. The implant set of claim 20, wherein the holding tool has a long hollow shaft through which a clamping element is guided that engages in the pulling thread.

22. The implant set of claim 20, wherein a laterally extending projection is provided at the rear end of the hollow shaft and has a predefined orientation with respect to the elongate gripper foot.

23. The implant set of claim 1, wherein the material used is a titanium alloy or pure titanium.

24. The implant set of claim 1, wherein the main bodies have different thicknesses in the range of 3 to 15 mm.

25. The implant set of claim 1, wherein the set additionally comprises a plurality of mirror-inverted main bodies.

26. The implant set of claim 1, wherein a laterally protruding fixing tongue is provided on a rear edge of the lateral side surface.

27. The implant set of claim 26, wherein the fixing tongue is configured to be changed in terms of its angle to the lateral side surface.

28. The implant set of claim 26, wherein the fixing tongue has a fastening hole, which has several defined receiving positions for a second fastening element.

29. The implant set of claim 28, wherein the receiving positions are configured for the polyaxial reception of a pars screw.

30. The implant set of claim 28, wherein the second fastening element comprises a pars screw.

31. An implant configured for insertion into the lamina of a vertebra comprising a main body with bearing surfaces configured to bear on the vertebra and a fastening device,
wherein the main body has a front surface, a rear surface, a lateral side surface and a medial side surface, and
wherein the lateral and medial side surfaces are arranged on opposite sides and face outwards of the main body, the medial side surface is offset rearwardly in relation to the lateral side surface, and the side surfaces are designed to bear on sectioned surfaces of the lamina, and a rearwardly protruding extension with a lateral bearing surface on a spinous process of the vertebra is arranged on the rear surface.

* * * * *